(12) United States Patent
Abramson

(10) Patent No.: US 9,763,767 B2
(45) Date of Patent: *Sep. 19, 2017

(54) SYSTEM AND METHOD FOR ALLEVIATING SLEEP APNEA

(71) Applicant: Michael T. Abramson, Boston, MA (US)

(72) Inventor: Michael T. Abramson, Boston, MA (US)

(*) Notice: Subject to any disclaimer, the term of this patent is extended or adjusted under 35 U.S.C. 154(b) by 542 days.

This patent is subject to a terminal disclaimer.

(21) Appl. No.: 14/463,871

(22) Filed: Aug. 20, 2014

(65) Prior Publication Data

US 2014/0352702 A1 Dec. 4, 2014

Related U.S. Application Data

(63) Continuation of application No. 12/903,669, filed on Oct. 13, 2010, now Pat. No. 8,844,537.

(51) Int. Cl.
A61F 5/56 (2006.01)
A61F 2/02 (2006.01)
(Continued)

(52) U.S. Cl.
CPC ............ *A61F 2/025* (2013.01); *A61B 5/4809* (2013.01); *A61B 5/4818* (2013.01);
(Continued)

(58) Field of Classification Search
CPC ........ A61N 2/004; A61N 2/02; A61B 5/4809; A61B 5/4818; A61B 5/4836;
(Continued)

(56) References Cited

U.S. PATENT DOCUMENTS 2,904,033 A 9/1959 Shane
2,972,657 A 2/1961 Stemke
(Continued)

FOREIGN PATENT DOCUMENTS

DE 2450098 A1 4/1976
DE 2553244 A1 5/1977
(Continued)

OTHER PUBLICATIONS

Cameron et al., "Micromodular Implants to Provide Electrical Stimulation of Paralyzed Muscles and Limbs", IEEE Transactions on Biomedical Enginerring, vol. 44, No. 9, Sep. 1997, pp. 781-790.
(Continued)

*Primary Examiner* — Tarla Patel
(74) *Attorney, Agent, or Firm* — Michael T. Abramson

(57) ABSTRACT

A system and method for controlling a device to alleviate sleep apnea comprises determining whether a user of the device is asleep by a microcontroller operatively connected to the device. Using a sensor operatively connected to the microcontroller, it is determined whether a breathing anomaly of the user is detected while the user is asleep. An electromagnet operatively connected to the device generates an electromagnetic field to widen an airway of the user in response to detecting the breathing anomaly while the user is asleep.

21 Claims, 10 Drawing Sheets

(51) Int. Cl.
  *A61N 2/02* (2006.01)
  *A61B 5/00* (2006.01)
  *A61N 2/00* (2006.01)
  *A61F 2/48* (2006.01)
  *A61B 5/024* (2006.01)
  *A61B 5/0488* (2006.01)
  *A61B 5/08* (2006.01)
  *A61B 5/1455* (2006.01)

(52) U.S. Cl.
  CPC .............. *A61B 5/4836* (2013.01); *A61F 5/56* (2013.01); *A61N 2/004* (2013.01); *A61N 2/02* (2013.01); *A61B 5/024* (2013.01); *A61B 5/0488* (2013.01); *A61B 5/08* (2013.01); *A61B 5/14551* (2013.01); *A61B 2562/0204* (2013.01); *A61B 2562/0219* (2013.01); *A61F 2002/482* (2013.01)

(58) Field of Classification Search
  CPC ........ A61B 2562/0204; A61B 5/14551; A61B 5/0488; A61B 5/024; A61B 2562/0219; A61B 5/08; A61F 5/56; A61F 2002/482
  USPC ................ 128/848, 850, 852, 859, 860–863; 600/12, 13, 373, 380, 422, 423, 427, 534, 600/26; 607/42, 62, 65, 134, 48
  See application file for complete search history.

(56) References Cited

U.S. PATENT DOCUMENTS

| | | |
|---|---|---|
| 3,259,873 A | 7/1966 | Parkinson et al. |
| 3,268,846 A | 8/1966 | Morey |
| 3,559,638 A | 2/1971 | Potter |
| 3,595,228 A | 7/1971 | Simon et al. |
| 3,611,801 A | 10/1971 | Paine |
| 3,726,270 A | 4/1973 | Griffis et al. |
| 3,802,417 A | 4/1974 | Lang |
| 3,817,246 A | 6/1974 | Weigl |
| 3,876,964 A | 4/1975 | Balaster et al. |
| 3,882,847 A | 5/1975 | Jacobs |
| 3,903,875 A | 9/1975 | Hughes |
| 3,914,994 A | 10/1975 | Banner |
| 3,926,175 A | 12/1975 | Allen et al. |
| 3,932,054 A | 1/1976 | McKelvey |
| 3,939,821 A | 2/1976 | Roth |
| 3,957,036 A | 5/1976 | Normann |
| 3,961,627 A | 6/1976 | Ernst et al. |
| 3,985,467 A | 10/1976 | Lefferson |
| 3,986,493 A | 10/1976 | Hendren, III |
| 3,989,037 A | 11/1976 | Franetzki |
| 4,006,634 A | 2/1977 | Billette et al. |
| 4,024,855 A | 5/1977 | Bucalo |
| 4,050,458 A | 9/1977 | Friend |
| 4,053,952 A | 10/1977 | Goldstein |
| 4,077,404 A | 3/1978 | Elam |
| 4,083,245 A | 4/1978 | Osborn |
| 4,133,735 A | 1/1979 | Afromowitz et al. |
| 4,146,885 A | 3/1979 | Lawson, Jr. |
| 4,205,678 A | 6/1980 | Adair |
| 4,206,754 A | 6/1980 | Cox et al. |
| 4,244,362 A | 1/1981 | Anderson |
| 4,258,705 A | 3/1981 | Sorensen et al. |
| 4,304,227 A | 12/1981 | Samelson |
| 4,312,235 A | 1/1982 | Daigle |
| 4,320,766 A | 3/1982 | Alihanka et al. |
| 4,322,594 A | 3/1982 | Brisson |
| 4,340,038 A | 7/1982 | McKean |
| 4,353,372 A | 10/1982 | Ayer |
| 4,364,377 A | 12/1982 | Smith |
| 4,365,636 A | 12/1982 | Barker |
| 4,370,984 A | 2/1983 | Cartmell |
| 4,381,788 A | 5/1983 | Douglas |
| 4,387,722 A | 6/1983 | Kearns |
| 4,414,982 A | 11/1983 | Durkan |
| 4,433,693 A | 2/1984 | Hochstein |
| 4,440,177 A | 4/1984 | Anderson et al. |
| 4,445,501 A | 5/1984 | Bresler |
| 4,448,058 A | 5/1984 | Jaffe et al. |
| 4,475,559 A | 10/1984 | Horn |
| 4,481,944 A | 11/1984 | Bunnell |
| 4,499,914 A | 2/1985 | Schebler |
| 4,506,666 A | 3/1985 | Durkan |
| 4,519,399 A | 5/1985 | Hori |
| 4,541,429 A | 9/1985 | Prosl et al. |
| 4,550,615 A | 11/1985 | Grant |
| 4,550,726 A | 11/1985 | McEwen |
| 4,558,710 A | 12/1985 | Eichler |
| 4,570,631 A | 2/1986 | Durkan |
| 4,576,179 A | 3/1986 | Manus et al. |
| 4,580,575 A | 4/1986 | Birnbaum et al. |
| 4,586,106 A | 4/1986 | Frazier |
| 4,595,016 A | 6/1986 | Fertig et al. |
| 4,595,390 A | 6/1986 | Hakim et al. |
| 4,602,644 A | 7/1986 | DiBenedetto et al. |
| 4,619,270 A | 10/1986 | Margolis et al. |
| 4,630,614 A | 12/1986 | Atlas |
| 4,648,396 A | 3/1987 | Raemer |
| 4,648,407 A | 3/1987 | Sackner |
| 4,655,213 A | 4/1987 | Rapoport et al. |
| 4,659,872 A | 4/1987 | Dery et al. |
| 4,665,926 A | 5/1987 | Leuner et al. |
| 4,677,975 A | 7/1987 | Edgar et al. |
| 4,686,974 A | 8/1987 | Sato et al. |
| 4,686,999 A | 8/1987 | Snyder et al. |
| 4,693,236 A | 9/1987 | Leprevost |
| 4,694,839 A | 9/1987 | Timme |
| 4,715,367 A | 12/1987 | Crossley |
| 4,723,543 A | 2/1988 | Beran |
| 4,738,266 A | 4/1988 | Thatcher |
| 4,747,403 A | 5/1988 | Gluck et al. |
| 4,748,293 A | 5/1988 | Kikuchi et al. |
| 4,777,962 A | 10/1988 | Watson et al. |
| 4,777,963 A | 10/1988 | McKenna |
| 4,795,314 A | 1/1989 | Prybella et al. |
| 4,802,485 A | 2/1989 | Bowers et al. |
| 4,803,471 A | 2/1989 | Rowland |
| 4,819,629 A | 4/1989 | Jonson |
| 4,823,788 A | 4/1989 | Smith et al. |
| 4,825,802 A | 5/1989 | Le Bec |
| 4,827,922 A | 5/1989 | Champain et al. |
| 4,827,935 A | 5/1989 | Geddes et al. |
| 4,830,008 A | 5/1989 | Meer |
| 4,831,240 A | 5/1989 | Davis |
| 4,838,258 A | 6/1989 | Dryden et al. |
| 4,844,085 A | 7/1989 | Gattinoni |
| 4,860,766 A | 8/1989 | Sackner |
| 4,870,960 A | 10/1989 | Hradek |
| 4,887,607 A | 12/1989 | Beatty |
| 4,915,103 A | 4/1990 | Visveshwara et al. |
| 4,928,684 A | 5/1990 | Breitenfelder et al. |
| 4,938,210 A | 7/1990 | Shene |
| 4,938,212 A | 7/1990 | Snook et al. |
| 4,957,107 A | 9/1990 | Sipin |
| 4,960,118 A | 10/1990 | Pennock |
| 4,971,065 A | 11/1990 | Pearce |
| 4,972,842 A | 11/1990 | Korten et al. |
| 4,978,323 A | 12/1990 | Freedman |
| 4,982,738 A | 1/1991 | Griebel |
| 4,986,269 A | 1/1991 | Hakkinen |
| 4,989,599 A | 2/1991 | Carter |
| 5,019,372 A | 5/1991 | Folkman et al. |
| 5,024,219 A | 6/1991 | Dietz |
| 5,046,491 A | 9/1991 | Derrick |
| 5,048,515 A | 9/1991 | Sanso |
| 5,052,400 A | 10/1991 | Dietz |
| 5,056,519 A | 10/1991 | Vince |
| 5,058,600 A | 10/1991 | Schechter et al. |
| 5,063,922 A | 11/1991 | Hakkinen |
| 5,063,938 A | 11/1991 | Beck et al. |
| 5,065,756 A | 11/1991 | Rapoport |
| 5,069,222 A | 12/1991 | McDonald, Jr. |
| 5,090,248 A | 2/1992 | Cimmino et al. |

(56) References Cited

U.S. PATENT DOCUMENTS

| | | |
|---|---|---|
| 5,095,900 A | 3/1992 | Fertig et al. |
| 5,099,837 A | 3/1992 | Russel, Sr. et al. |
| 5,105,354 A | 4/1992 | Nishimura |
| 5,107,830 A | 4/1992 | Younes |
| 5,107,831 A | 4/1992 | Halpern et al. |
| 5,123,425 A | 6/1992 | Shannon, Jr. et al. |
| 5,129,390 A | 7/1992 | Chopin et al. |
| 5,134,995 A | 8/1992 | Gruenke et al. |
| 5,146,918 A | 9/1992 | Kallok et al. |
| 5,148,802 A | 9/1992 | Sanders et al. |
| 5,161,541 A | 11/1992 | Bowman et al. |
| 5,170,798 A | 12/1992 | Riker |
| 5,174,287 A | 12/1992 | Kallok et al. |
| 5,176,618 A | 1/1993 | Freedman |
| 5,178,138 A | 1/1993 | Walstrom et al. |
| 5,178,151 A | 1/1993 | Sackner |
| 5,178,156 A | 1/1993 | Takishima et al. |
| 5,190,048 A | 3/1993 | Wilkinson |
| 5,193,539 A | 3/1993 | Schulman et al. |
| 5,193,540 A | 3/1993 | Schulman et al. |
| 5,195,528 A | 3/1993 | Hok |
| 5,199,424 A | 4/1993 | Sullivan et al. |
| 5,203,343 A | 4/1993 | Axe et al. |
| 5,220,918 A | 6/1993 | Heide et al. |
| 5,231,983 A | 8/1993 | Matson et al. |
| 5,233,983 A | 8/1993 | Markowitz |
| 5,238,006 A | 8/1993 | Markowitz |
| 5,239,994 A | 8/1993 | Atkins |
| 5,239,995 A | 8/1993 | Estes et al. |
| 5,245,995 A | 9/1993 | Sullivan et al. |
| 5,259,373 A | 11/1993 | Gruenke et al. |
| 5,265,624 A | 11/1993 | Bowman |
| 5,277,193 A | 1/1994 | Takishima et al. |
| 5,280,784 A | 1/1994 | Kohler |
| 5,293,864 A | 3/1994 | McFadden |
| 5,295,491 A | 3/1994 | Gevins |
| 5,303,698 A | 4/1994 | Tobia et al. |
| 5,303,700 A | 4/1994 | Weismann et al. |
| 5,311,875 A | 5/1994 | Stasz |
| 5,312,439 A | 5/1994 | Loeb |
| 5,313,937 A | 5/1994 | Zdrojkowski |
| 5,322,057 A | 6/1994 | Raabe et al. |
| 5,327,899 A | 7/1994 | Harris et al. |
| 5,329,931 A | 7/1994 | Clauson et al. |
| 5,335,654 A | 8/1994 | Rapoport |
| 5,335,657 A | 8/1994 | Terry, Jr. et al. |
| 5,344,438 A | 9/1994 | Testerman et al. |
| 5,353,788 A | 10/1994 | Miles |
| 5,360,008 A | 11/1994 | Campbell, Jr. |
| 5,361,775 A | 11/1994 | Remes et al. |
| 5,373,842 A | 12/1994 | Olsson et al. |
| 5,373,859 A | 12/1994 | Forney |
| 5,388,571 A | 2/1995 | Roberts et al. |
| 5,394,882 A | 3/1995 | Mawhinney |
| 5,398,682 A | 3/1995 | Lynn |
| 5,400,777 A | 3/1995 | Olsson et al. |
| 5,404,871 A | 4/1995 | Goodman et al. |
| 5,413,111 A | 5/1995 | Wilkinson |
| 5,433,193 A | 7/1995 | Sanders et al. |
| 5,438,980 A | 8/1995 | Phillips |
| 5,443,061 A | 8/1995 | Champain et al. |
| 5,443,075 A | 8/1995 | Holscher |
| 5,448,996 A | 9/1995 | Bellin et al. |
| 5,458,137 A | 10/1995 | Axe et al. |
| 5,465,734 A | 11/1995 | Alvarez et al. |
| 5,476,483 A | 12/1995 | Bornzin et al. |
| 5,479,920 A | 1/1996 | Piper et al. |
| 5,479,939 A | 1/1996 | Ogino |
| 5,483,969 A | 1/1996 | Testerman et al. |
| 5,490,502 A | 2/1996 | Rapoport et al. |
| 5,503,146 A | 4/1996 | Froehlich et al. |
| 5,507,282 A | 4/1996 | Younes |
| 5,509,404 A | 4/1996 | Lloyd et al. |
| 5,509,414 A | 4/1996 | Hok |
| 5,513,631 A | 5/1996 | McWilliams |
| 5,522,382 A | 6/1996 | Sullivan et al. |
| RE35,295 E | 7/1996 | Estes et al. |
| 5,535,738 A | 7/1996 | Estes et al. |
| 5,535,739 A | 7/1996 | Rapoport et al. |
| 5,540,219 A | 7/1996 | Mechlenburg et al. |
| 5,540,220 A | 7/1996 | Gropper et al. |
| 5,540,732 A | 7/1996 | Testerman |
| 5,540,733 A | 7/1996 | Testerman et al. |
| 5,546,933 A | 8/1996 | Rapoport et al. |
| 5,546,952 A | 8/1996 | Erickson |
| 5,549,106 A | 8/1996 | Gruenke et al. |
| 5,549,655 A | 8/1996 | Erickson |
| 5,549,656 A | 8/1996 | Reiss |
| 5,551,419 A | 9/1996 | Froehlich et al. |
| 5,570,682 A | 11/1996 | Johnson |
| 5,588,439 A | 12/1996 | Hollub |
| 5,591,216 A | 1/1997 | Testerman et al. |
| 5,598,838 A | 2/1997 | Servidio et al. |
| 5,605,151 A | 2/1997 | Lynn |
| 5,608,647 A | 3/1997 | Rubsamen et al. |
| 5,630,411 A | 5/1997 | Holscher |
| 5,642,730 A | 7/1997 | Baran |
| 5,647,351 A | 7/1997 | Weismann et al. |
| 5,649,540 A | 7/1997 | Alvarez et al. |
| 5,652,566 A | 7/1997 | Lambert |
| 5,655,520 A | 8/1997 | Howe et al. |
| 5,660,171 A | 8/1997 | Kimm et al. |
| 5,666,946 A | 9/1997 | Langenback |
| 5,671,733 A | 9/1997 | Raviv et al. |
| 5,697,076 A | 12/1997 | Troyk et al. |
| 5,701,883 A | 12/1997 | Hete et al. |
| 5,704,345 A | 1/1998 | Berthon-Jones |
| 5,730,121 A | 3/1998 | Hawkins, Jr. et al. |
| 5,769,084 A | 6/1998 | Katz et al. |
| 5,776,073 A | 7/1998 | Garfield et al. |
| 5,792,067 A | 8/1998 | Karell |
| 5,795,304 A | 8/1998 | Sun et al. |
| 5,797,852 A | 8/1998 | Karakasoglu et al. |
| 5,803,066 A | 9/1998 | Rapoport et al. |
| 5,817,135 A | 10/1998 | Cooper et al. |
| 5,844,996 A | 12/1998 | Enzmann et al. |
| 5,845,636 A | 12/1998 | Gruenke et al. |
| RE36,120 E | 3/1999 | Karell |
| 5,891,185 A | 4/1999 | Freed et al. |
| 5,911,218 A | 6/1999 | DiMarco |
| 5,953,713 A | 9/1999 | Behbehani et al. |
| 5,961,447 A | 10/1999 | Raviv et al. |
| 5,988,171 A | 11/1999 | Sohn et al. |
| 6,011,477 A | 1/2000 | Teodorescu et al. |
| 6,062,216 A | 5/2000 | Corn |
| 6,093,158 A | 7/2000 | Morris |
| 6,132,384 A | 10/2000 | Christopherson et al. |
| 6,138,675 A | 10/2000 | Berthon-Jones |
| 6,231,496 B1 | 5/2001 | Wilk et al. |
| 6,240,316 B1 | 5/2001 | Richmond et al. |
| 6,244,865 B1 | 6/2001 | Nelson et al. |
| 6,250,307 B1 | 6/2001 | Conrad et al. |
| 6,314,323 B1 | 11/2001 | Ekwall |
| 6,331,536 B1 | 12/2001 | Radulovacki et al. |
| 6,390,096 B1 | 5/2002 | Conrad et al. |
| 6,401,717 B1 | 6/2002 | Conrad et al. |
| 6,408,851 B1 | 6/2002 | Karell |
| 6,415,183 B1 | 7/2002 | Scheiner et al. |
| 6,415,796 B1 | 7/2002 | Conrad et al. |
| 6,432,956 B1 | 8/2002 | Dement et al. |
| 6,450,169 B1 | 9/2002 | Conrad et al. |
| 6,466,821 B1 | 10/2002 | Pianca et al. |
| 6,490,885 B1 | 12/2002 | Wilkinson |
| 6,519,493 B1 | 2/2003 | Florio et al. |
| 6,520,917 B1 | 2/2003 | Kunig et al. |
| 6,523,541 B2 | 2/2003 | Knudson et al. |
| 6,525,073 B2 | 2/2003 | Mendel et al. |
| 6,586,478 B2 | 7/2003 | Ackman et al. |
| 6,616,613 B1 | 9/2003 | Goodman |
| 6,636,767 B1 | 10/2003 | Knudson et al. |
| 6,641,542 B2 | 11/2003 | Cho et al. |
| 6,658,292 B2 | 12/2003 | Kroll et al. |
| 6,666,830 B1 | 12/2003 | Lehrman et al. |
| 6,881,192 B1 | 4/2005 | Park |

(56) References Cited

U.S. PATENT DOCUMENTS

| | | |
|---|---|---|
| 6,935,335 B1 | 8/2005 | Lehrman et al. |
| 6,955,172 B2 | 10/2005 | Nelson et al. |
| 7,073,505 B2 | 7/2006 | Nelson et al. |
| 7,077,143 B2 | 7/2006 | Knudson et al. |
| 7,077,144 B2 | 7/2006 | Knudson et al. |
| 7,179,229 B1 | 2/2007 | Koh |
| 7,188,627 B2 | 3/2007 | Nelson et al. |
| 7,363,926 B2 | 4/2008 | Pflueger et al. |
| 7,500,484 B2 | 3/2009 | Nelson et al. |
| 7,593,768 B1 | 9/2009 | Vasiliev et al. |
| 8,047,206 B2 | 11/2011 | Boucher et al. |
| 8,844,537 B1 * | 9/2014 | Abramson ............ A61N 2/004 128/848 |
| 2001/0047805 A1 | 12/2001 | Scarberry et al. |
| 2003/0036685 A1 | 2/2003 | Goodman |
| 2003/0130703 A1 | 7/2003 | Florio et al. |
| 2003/0153954 A1 | 8/2003 | Park et al. |
| 2004/0010180 A1 | 1/2004 | Scorvo |
| 2004/0112390 A1 | 6/2004 | Brooks et al. |
| 2004/0139975 A1 | 7/2004 | Nelson et al. |
| 2005/0092332 A1 | 5/2005 | Conrad et al. |
| 2005/0115561 A1 | 6/2005 | Stahmann et al. |
| 2005/0115572 A1 | 6/2005 | Brooks et al. |
| 2005/0121039 A1 | 6/2005 | Brooks et al. |
| 2005/0159637 A9 | 7/2005 | Nelson et al. |
| 2006/0005843 A9 | 1/2006 | Nelson et al. |
| 2006/0276855 A1 | 12/2006 | Klapproth et al. |
| 2007/0067004 A1 | 3/2007 | Boveja et al. |
| 2007/0261701 A1 | 11/2007 | Sanders |
| 2009/0038623 A1 | 2/2009 | Farbarik et al. |
| 2009/0322557 A1 | 12/2009 | Robb et al. |
| 2010/0157659 A1 | 6/2010 | Norman |
| 2010/0201476 A1 | 8/2010 | Jha et al. |
| 2010/0249652 A1 | 9/2010 | Rush et al. |
| 2010/0249756 A1 | 9/2010 | Koh |
| 2010/0250911 A1 | 9/2010 | Trebbels et al. |

FOREIGN PATENT DOCUMENTS

| | | |
|---|---|---|
| DE | 4307262 A1 | 9/1994 |
| EP | 0366127 B1 | 5/1990 |
| EP | 0404427 B1 | 12/1990 |
| WO | 9837926 A1 | 9/1998 |
| WO | 9843700 A1 | 10/1998 |
| WO | 9843701 A1 | 10/1998 |
| WO | 2004084709 A2 | 10/2004 |

OTHER PUBLICATIONS

Block et al. "Factors Influencing Upper Airway Closure", Chest vol. 86, No. 1, Jul. 1984, pp. 114-122.

* cited by examiner

SYSTEM AND METHOD FOR ALLEVIATING SLEEP APNEA

RELATED CASES

This application is a Continuation of U.S. patent application Ser. No. 12/903,669 filed on 13 Oct. 2010 by Michael T. Abramson, entitled "System and Method for Alleviating Sleep Apnea", the contents of which are all incorporated by reference.

FIELD OF THE DISCLOSURE

The present disclosure generally relates to sleep apnea, and, more particularly, to alleviating sleep apnea using an implantable device.

BACKGROUND OF THE DISCLOSURE

Sleep apnea is a common but serious and potentially life-threatening condition affecting millions of Americans. Sleep apnea is a breathing disorder characterized by brief interruptions (e.g., 10 seconds or more) of breathing during sleep. There are two types of sleep apnea: central and obstructive. Central sleep apnea, which is relatively rare, occurs when the brain fails to send the appropriate signal to the breathing muscles to initiate respirations.

Obstructive sleep apnea (OSA) is far more common. FIG. 1A is an anatomic view of a person with an open upper airway. Normally, the muscles of the upper part of the throat keep the airway open to permit air flow into the lungs. When the muscles of the upper airway relax and sag, the relaxed tissues may vibrate as air flows past the tissues during breathing, resulting in snoring. In more serious cases, as seen from FIG. 1B, the airway becomes blocked, making breathing labored and noisy, or even stopping it altogether. In a given night, the number of involuntary breathing pauses or "apneic events" can be quite frequent. A lack of air intake into the lungs may result in lower levels of oxygen and increased levels of carbon dioxide in the blood. The altered levels of oxygen and carbon dioxide alert the brain to resume breathing and may cause the sleeper to struggle and gasp for air. Breathing will then resume, often followed by continued apneic events. There are potentially damaging effects to the heart and blood vessels due to abrupt compensatory swings in blood pressure. Upon each event, the sleeping person will be partially aroused from sleep, resulting in a greatly reduced quality of sleep. The frequent interruptions of deep, restorative sleep may lead to early morning headaches, excessive daytime sleepiness, depression, irritability, and learning and memory difficulties. OSA may also increase the risk of heart attacks, hypertension, and strokes.

One solution for easing the onset of OSA is the Continuous Positive Airway Pressure (CPAP) machine. The CPAP machine accomplishes this by delivering a constant stream of compressed air at a prescribed pressure level (also called the titrated pressure) via a hose to a nasal pillow, nose mask or full-face mask. Thus, the airway is splinted and remains open under the air pressure, resulting in a reduction and/or prevention of apneas and hypopneas. However, while effective, the CPAP machine suffers from numerous disadvantages. For example, having to wear a mask strapped around one's head may be cumbersome and uncomfortable. Additionally, the CPAP machine is very noisy which may make it difficult for the user (or anyone nearby) to sleep. Moreover, aerophagia or swallowing too much air, a common cause of gas in the stomach and belching, can be caused by the CPAP.

Another solution for easing the onset of OSA involves surgery. For example, uvulopalatopharyngoplasty, tonsillectomy, surgery to correct severe retrognathia and tracheostomy may be conducted. While these procedures may be effective in some patients, there is a potential for scarring of tissue, which may actually exacerbate the problem.

Yet another solution for easing the onset of OSA involves the surgical implantation of magnets within the human body. An example of such a solution is described by Nelson et al., in U.S. Pat. No. 7,188,627 entitled, MAGNETIC FORCE DEVICES, SYSTEMS, AND METHODS FOR RESISTING TISSUE COLLAPSE WITHIN THE PHARYNGEAL CONDUIT, filed on Sep. 6, 2003. By implanting similarly polarized magnets on opposing sides in a tissue region in a lateral pharyngeal wall along a pharyngeal conduit, the repulsion of the magnets may be enough to resist collapse of the soft wall tissue, thereby resisting the cause of OSA. However, this approach suffers from numerous disadvantages. For instance, one disadvantage is that the opposing magnetic forces are constantly being applied. As such, for example, the user will feel the repulsion even when the user is awake. Moreover, the constant application of the opposing magnetic forces would make eating and swallowing very difficult and uncomfortable. Another disadvantage is that because the opposing magnetic forces are constantly being applied, the user may accidentally come into contact with other ferromagnetic material which may also cause discomfort. Yet another disadvantage is that the constant application of force against the tissue may constrict the blood flow out of the surrounding tissue area, which may cause cell death. Yet another disadvantage is that while it may be possible to adjust the strength of the magnets before they are surgically implanted, there is no way to adjust the strength of the magnets after they are surgically implanted, except for surgically removing and/or replacing the magnets.

Therefore, there remains a need for an intelligent device for alleviating OSA that is not cumbersome to the user.

BRIEF SUMMARY OF DISCLOSURE

The disclosure overcomes the disadvantages of the prior art by providing a system and method for alleviating sleep apnea using a surgically implantable intelligent device(s). The devices may be strategically implanted in the human body to provide relief from obstructive sleep apnea (OSA). In one embodiment, the devices are magnets (e.g., electromagnets) controlled with one or more potentiometers (pots). One of the characteristics of pots is their ability to take an input from a power source and to output a variable resistance. Since the amount of current applied from a power/current source to an electromagnet is one of the variables affecting its strength (i.e., magnetic field), the pot may be used to control the strength of the device via the electromagnet (e.g., by varying the resistance of the pot). For example, Ohm's law states that the current through a conductor between two points is directly proportional to the potential difference or voltage across the two points, and inversely proportional to the resistance between them. The mathematical equation that describes this relationship is $I=V/R$, where I is the current through the resistance in units of amperes, V is the potential difference measured across the resistance in units of volts, and R is the resistance of the conductor in units of ohms. As such, unlike the prior art which maintains a constant magnetic field, by using the pot to vary its resistance R, it is possible to control the current I received by the electromagnet, thereby enabling variable strength of the device, and even enabling an "off" or "user is awake" mode state of the device when the device is not required (e.g., when the user is awake) by eliminating or substantially reducing the current I received by the electromagnet.

In another embodiment, the pot may be a digital pot (digipot) comprising a non-volatile memory that may be used to retain a last programmed resistance value after the digipot has been power cycled (e.g., turned off and on). The digipot may also be controlled by a microcontroller/microprocessor to retain a resistance value with which to initialize the digipot. Advantageously, the device may be programmed (and reprogrammed) with specific prescribed resistance values to alter the strength of the electromagnetic field. Therefore, should a patient suffering from OSA require a stronger or weaker electromagnetic field to alleviate the OSA, the digipot and/or the microcontroller controlling the digipot may be reprogrammed and controlled without requiring further surgery to alter or change the device.

In an alternative embodiment, the device may further comprise one or more sensors, which may be used, for example, to determine when a user of the device is asleep. For instance, the device may be operatively connected to a sensor (e.g., accelerometer) configured to determine whether the patient is vertical (e.g., sitting up/standing) possibly indicting that the patient is awake or whether the patient is horizontal (e.g., laying down) possibly indicting that the patient is asleep or at least attempting to sleep. Data detected from the sensors may be used to aid in the determination of whether the user is asleep. Another type of sensor may be a myoelectric sensor configured for use with an electromyography (EMG) to detect the electrical potential generated by muscle cells when those cells are electrically or neurologically activated. For example, it may be possible to detect when a patient is about to swallow by detecting the electrical potential generated by the muscle cells involved in the act of swallowing when those cells are activated. Advantageously, should the device currently be generating an electromagnetic field while the patient is sleeping, the device may temporarily become inactive or lessen the strength of the electromagnetic field upon sensing that the patient is about to swallow, thereby lessening any potentially uncomfortable sensations felt by the patient that may occur due to the opposition of the force of the device during the act of swallowing. Once the sensor has detected the act of swallowing has completed, the device may resume its normal operation (e.g., whatever the electromagnetic field strength or state was prior to the reaction of the patient/user swallowing).

BRIEF DESCRIPTION OF THE DRAWINGS

The above and further advantages of the disclosure may be better understood by referring to the following description in conjunction with the accompanying drawings in which like reference numerals indicate identically or functionally similar elements.

DETAILED DESCRIPTION OF AN ILLUSTRATIVE EMBODIMENT

Electromagnet

A magnet, which is well known to those skilled in the art, is a material or object that produces a magnetic field. For example, a magnetic field may produce a force that "pulls" on ferromagnetic materials, such as iron, nickel, cobalt, some alloys of rare earth metals, and some naturally occurring minerals such as lodestone, and attracts or repels other magnets. A permanent magnet is an object made from a material that is magnetized and creates its own persistent magnetic field. Materials that can be magnetized are called ferromagnetic.

Figure 2:
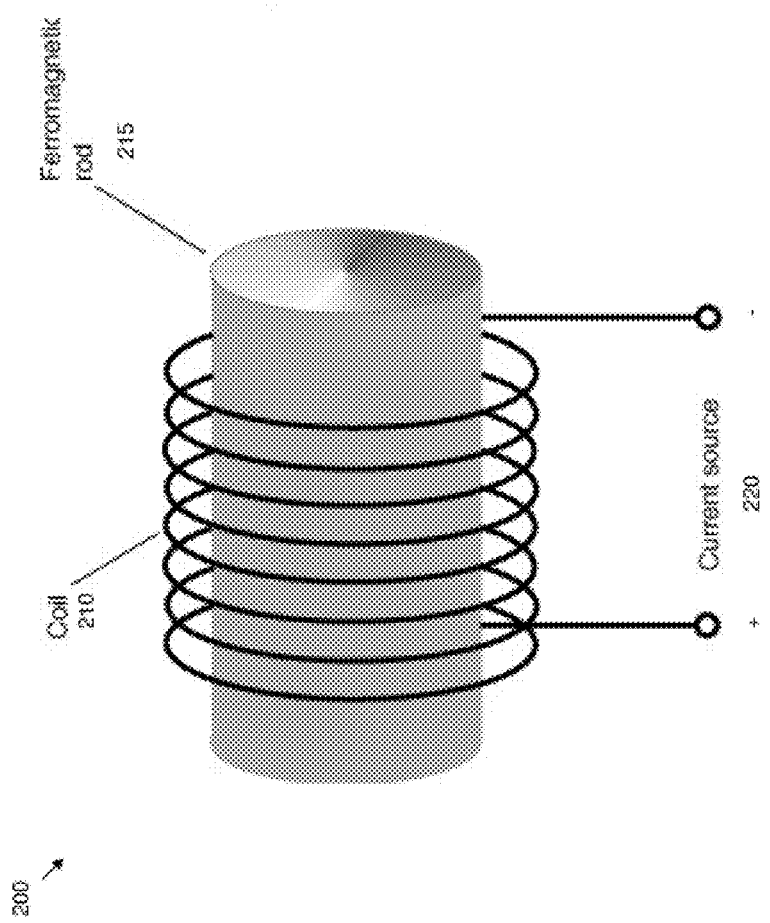
FIG. 2 is a schematic block diagram of an electromagnet that may be advantageously used with the present disclosure.

A similar magnetic field, e.g., an electromagnetic field, may also be produced using, e.g., an electromagnet, which is well known to those skilled in the art. As such, the terms magnetic field and electromagnetic field may be used interchangeably. FIG. 2 is a schematic block diagram of an electromagnet that may be advantageously used with the present disclosure. Broadly described for simplicity purposes, an electromagnet may be described in part as, e.g., a wire that has been coiled into one or more loops. For example, a coil 210 forming the shape of a straight tube is known as a solenoid. Another example is when a solenoid is bent into a donut shape so that the ends meet is known as a toroid. As can be appreciated by those skilled in the art, materials other than a wire capable of conducting a current may be used to create coil 210 as well. When a power or current source 220, e.g., from a battery, flows through the wire, a magnetic field is generated. While a battery is illustratively described as the power source, those skilled the art will recognize that other powers sources, such as a fuel cell, induction coil, capacitor and/or the like, and rechargeable power sources, may also be used. The magnetic field is concentrated near and inside the coil, and its field lines are very similar to those of a magnet. Notably, the magnetic field "disappears" when the current ceases from power source 220. If the wire it is wrapped around a soft ferromagnetic material, such as an iron rod or other ferromagnetic rod 215, the net field produced can be significantly increased due to the high magnetic permeability of the ferromagnetic material. This is called a ferromagnetic-core or iron-core electromagnet. Advantageously, because the net field produced by a ferromagnetic-core can be significantly increased, less current from the power source may be required to generate a desired electromagnetic field, thereby increasing the life of the power source. While an illustrative and simplified electromagnet is shown in FIG. 2 for simplicity, those skilled in the art will recognize that other electromagnet configurations may be used without departing from the scope of the present disclosure.

Potentiometer

A potentiometer (pot) is well known to those skilled in the art. A pot may be broadly described as, e.g., a three-terminal resistor with a sliding contact that forms an adjustable voltage divider. When only two terminals are used, e.g., one side and a wiper, a pot may act as a variable resistor or rheostat. A pot may have, e.g., a linear or logarithmic relationship between the slider position and the resistance. A linear (taper) pot has a resistive element of a constant cross-section, resulting in a device where the resistance between the contact (wiper) and one end terminal is proportional to the distance between them. A logarithmic (taper) pot has a resistive element that either "tapers" in from one end to the other, or is made from a material of which the resistance varies from one end to the other. This results in a device where output voltage is a logarithmic function of the mechanical angle of the pot. Other types of pots, including a membrane pot, and a digital pot, are also well known in the art and may be used in varying embodiments of the disclosure.

Figure 3:
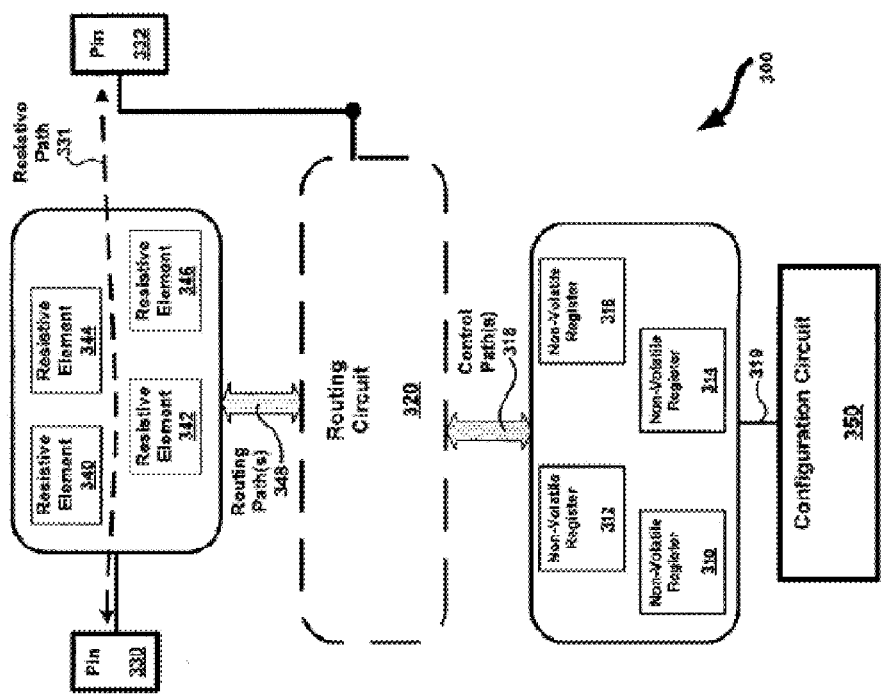
FIG. 3 is a schematic block diagram of a digital potentiometer that may be advantageously used with the present disclosure.

In a preferred embodiment, a digital pot (digipot) is used for the pot. FIG. 3 is a schematic block diagram of a digipot that may be advantageously used with the present disclosure. Broadly described, a digipot is an electronic component that mimics the functions of analog pots. Unlike traditional analog pot which may be adjusted mechanically, the resistance between two terminals may be adjusted with digipots, for instance, using a Serial Peripheral Interface (SPI) bus connection from a microcontroller or other software serial interfaces or digital input signals. A digipot presents advantages over an analog pot, for example, because of its higher resolution, its ability to store more than one wiper position, and its cost-effectiveness in implementing. Another advantage is that some digipots comprise non-volatile memory, so that they retain their last programmed position after they have been power cycled (e.g., powered down and powered up). For example, a digipot, such as the one described in U.S. patent application Ser. No. 12/653,897, published on Jun. 24, 2010 by Norman, may be programmable and reprogrammable using non-volatile registers 310-316. As such, the application of a voltage difference to one or more non-volatile registers can modify resistive path 331, thereby changing the resistance of the digipot. Illustratively, the resistive path 331 for the digipot may be dynamically set in real-time. Furthermore, as noted above, a digipot may maintain the programmed settings, even through power cycles, since the registers are non-volatile. Thus, after the digipot has been programmed, e.g., using a configuration circuit 350 or microcontroller, non-volatile registers 310-316 of the digipot may be configured to select resistive path 331 instantaneously (or substantially instantaneously) to power-up.

According to an illustrative embodiment, configuration circuit 350 may comprise logic to configure a subset of non-volatile registers 310-316 to determine a resistance for resistive path 331. In operation, configuration circuit 350 may generate and transmit configuration signals along configuration signal path(s) 319. In some examples, the configuration signals may include write and/or read voltage signals for programming and re-programming non-volatile registers 310-316 to generate control data signals. One or more control data signals may be transmitted over control path(s) 318 to routing circuit 320. In response to the control data signals, routing circuit 320 may be configured to select one or more routing path(s) through which one or more of resistive elements 340-346 (e.g., resistive memory elements) may be used to form resistive path 331. Routing circuit 320 may comprise, for example, switches (e.g., electronic switches) or transistors, as can be appreciated by those skilled in the art. In some examples, one or more of resistive elements 340-346 may comprise include resistive memory element, such as third dimensional memory elements. That is, one or more of resistive elements 340-346 may be fabricated back-end-of-the-line (BEOL) above active circuitry operative to access the resistive memory elements. In some embodiments, one or more resistive memory elements may have an adjustable resistance, while in other embodiments, one or more resistive memory elements may have a static resistance value. In various embodiments, resistive elements 340-346 may comprise any material suitable to form, for example, resistors.

By programming specific information into non-volatile registers 310-316, the desired combination of resistive elements 340-346 to establish a resistive path 331 between pin 330 and pin 332 may be accomplished. Some of the various elements depicted in FIG. 3 may be implemented using either hardware or software (e.g., firmware), or both. For example, a microcontroller, described in greater detail below, may be used to program and control the digipot. At least a portion of the hardware implementation may be implemented using fabricated front-end-of-the-line (FEOL) circuitry. While FIG. 3 depicts a particular configuration and implementation of a digipot, those skilled in the art will appreciate that various other configurations and implementations may be used without departing from the scope of the disclosure. For example, according to embodiments of the present disclosure, the pot may further comprise or be configured and implemented with a differential sensor input circuit to reject, amplify, and digitize noise. As such, those skilled in the art will appreciate that any pot, digital or otherwise, and any configuration and implementation therein capable of carrying out the functions of the disclosure may be used without departing from the scope of the disclosure.

Microcontroller

Figure 4:
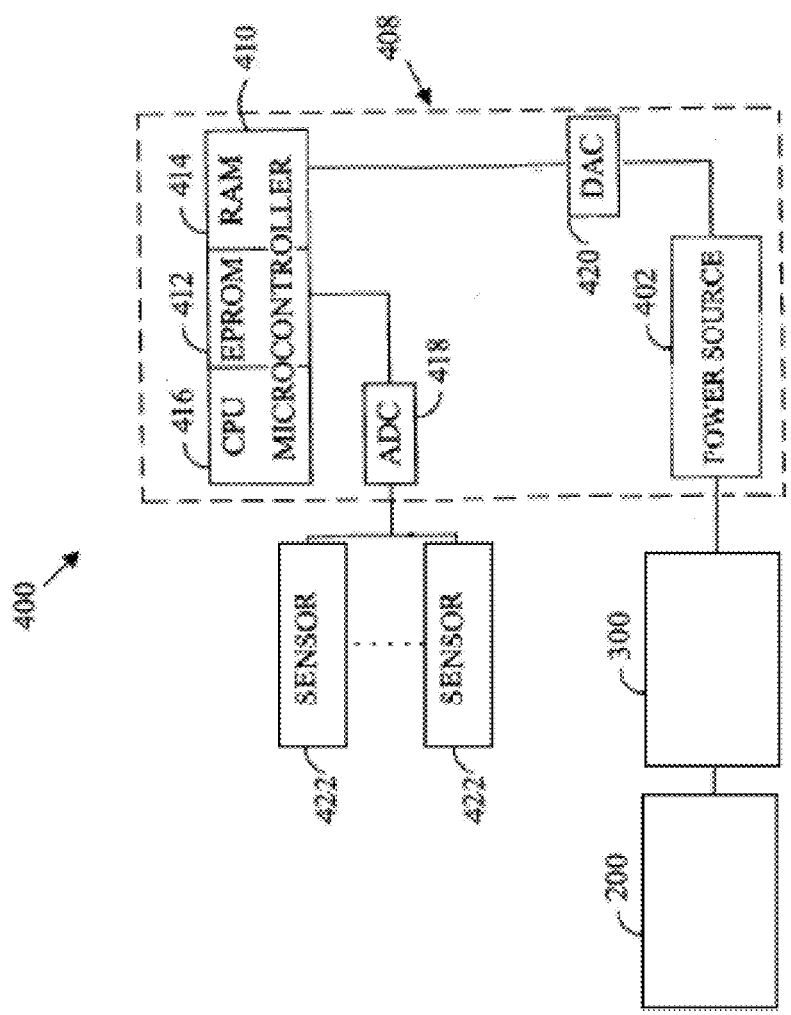
FIG. 4 is a schematic block diagram of a control unit that may be advantageously used with the present disclosure.

FIG. 4 is a schematic block diagram of a control unit 408 comprising an illustrative microcontroller 410 that may be advantageously used with the present disclosure. Microcontrollers may be used to automatically control devices, such as an implantable medical device. Mixed signal microcontrollers are common, integrating analog components needed to control non-digital electronic systems. The microcontroller may comprise a differential amplifier (e.g., to amplify raw EMG signals as acquired by electrodes/sensor(s) 422), a filter (e.g., low pass filter to distinguish a signal from noise), an AC coupled amplifier (e.g., to compensate any attenuation caused by the filter), an RMS to DC converter (e.g., to minimize patient-to-patient variations in signals received from sensors), an in-circuit programming and debugging support, discrete input and output bits allowing control and/or detection of a logic state of an individual package pin, a (micro) processor (e.g., a central processing unit (CPU) 416), a volatile and/or non-volatile memory (e.g., EPROM 412, EEPROM, ROM, or Flash memory, etc., e.g., for program and operating parameter storage, and/or a RAM 414), and programmable peripherals (e.g., timers, event counters, pulse width modulation (PWM) generators, etc.).

Typical input and output devices may comprise switches and/or sensors (e.g., bio or other types of data sensors, etc.) 422 to detect data such as temperature, blood oxygen levels, nerve impulses, humidity, light level, orientation, vibrations, etc. As will be discussed below, other types of sensors may also be used. The control unit 408 may also comprise an analog-to-digital converter (ADC) 418, for example, to convert analog signals output by sensing transducers (e.g., sensor(s) 422) to digital signals suitable for use by microcontroller 410. The control unit 408 may also comprise a digital-to-analog converter (DAC) 420, for example, to convert a digital output of the microcontroller 410 to an analog signal for operating the digipot 300 and electromagnet 200 via power source 402.

While one embodiment and configuration of a control unit is described as shown, it will be understood by those skilled in the art that any suitable implementation and/or configuration of a control unit capable of carrying out the functions of the disclosure may be used without departing from the scope of the present disclosure. For example, different microcontroller models such as those available from Texas Instruments, Inc. of Dallas, Tex., in addition to those described in Provisional U.S. Patent Application No. 602776 titled METHODS AND SYSTEMS FOR MODULATING THE VAGUS NERVE (10TH CRANIAL NERVE) TO PROVIDE THERAPY FOR NEUROLOGICAL, AND NEUROPSYCHIATRIC DISORDERS by Boveja et al., filed on Nov. 21, 2006 may also be used in the control unit in accordance with the present disclosure.

Sensors

As noted above, other types of sensors, such as blood oxygen level sensors and sleep sensors, may be used as an input or control signal for microcontroller 410 or other devices. An accelerometer (e.g., piezoelectric, piezoresistive and capacitive), for example, may also be used to detect an object's orientation (e.g., horizontal and/or vertical), motion, vibration, wind loads/gusts, air pressure, etc. For example, a microphone or accelerometer, both of which are well known to those skilled in the art, may be used as a vibration sensor to detect the vibrations associated with snoring.

Another example of a sensor is a myoelectric sensor/electrode. As can be appreciated by those skilled in the art, Electromyography (EMG) is a technique for evaluating and recording the electrical activity produced by, e.g., skeletal muscles. EMG may be performed using an instrument called an electromyograph, to produce a record called an electromyogram. An electromyograph detects the electrical potential, e.g., measured in microvolts, generated by muscle cells when these cells are electrically or neurologically activated. Generally, there are two kinds of EMG: surface EMG and intramuscular EMG. Typically, to perform intramuscular EMG, an electrode (e.g., a needle electrode) is inserted through the skin into the muscle tissue. The electrode may be crimped to provide stability and contact with the muscle tissue. In one embodiment, the myoelectric sensor (e.g., electrode) may comprise a biocompatible metal wire formed into a flat blade having a sharp tip and serrations along at least one edge. Alternatively, the electrode may be a round electrode, multi-filar electrode, etc. In another illustrative embodiment, the sensors may comprise microelectromechanical systems (MEMS), which are around 20 micrometers in size. An insulated lead (e.g., a 0.25 micron diameter platinum/iridium (Pt/Ir) Teflon-coated wire) may be attached to the blade, where the blade may be inserted through a small "slot" made in the muscle tissue, for example, by nerve/muscle graft surgeries. Each electrode might only give a local picture of the activity of the whole muscle. Because skeletal muscles differ in the inner structure, the electrode may be placed at various locations for accuracy.

A motor unit is defined as one motor neuron and the muscle fibers it innervates. When a motor unit fires, the impulse (e.g., action potential or a short-lasting event in which the electrical membrane potential of a cell rapidly rises and falls following a stereotyped trajectory) is carried down the motor neuron to the muscle. The area where the nerve contacts the muscle is called the neuromuscular junction, or the motor end plate. After the action potential is transmitted across the neuromuscular junction, an action potential is elicited in the innervated muscle fibers of that particular motor unit. Generally, the sum of all this electrical activity is known as a motor unit action potential (MUAP). This electrophysiological activity from multiple motor units is the signal typically evaluated during an EMG. The composition of the motor unit, the number of muscle fibers per motor unit, the metabolic type of muscle fibers and many other factors may affect the shape of the motor unit potentials in the myogram.

Muscle tissue at rest is "normally" electrically inactive. At rest, the electromyograph should detect no abnormal spontaneous activity (i.e., a muscle at rest should be electrically silent, with the possible exception of the area of the neuromuscular junction, which is, under normal circumstances, spontaneously active). When the muscle is voluntarily contracted, action potentials may be detected by the myosensor. As the strength of the muscle contraction is increased, more and more muscle fibers produce action potentials. When the muscle is fully contracted, there should appear a disorderly group of action potentials of varying rates and amplitudes (a complete recruitment and interference pattern). By using myosensors, it is possible to detect when a muscle is voluntarily contracting, such as when the muscles involved in, for example, swallowing or breathing.

Device for Alleviating Sleep Apnea

The disclosure overcomes the disadvantages of the prior art by providing a system and method for alleviating sleep apnea using a (surgically implantable) intelligent device(s). The devices may be strategically implanted in the human body to provide relief from obstructive sleep apnea (OSA). In one embodiment, the devices are magnets (e.g., electromagnets) controlled with one or more potentiometers (pots). One of the characteristics of pots is their ability to take an input from a power source and to output a variable resistance. Since the amount of current applied from a power/current source to an electromagnet is one of the variables affecting its strength (i.e., magnetic field), the pot may be used to control the strength of the device via the electromagnet (e.g., by varying the resistance of the pot). For example, as is well known to those skilled in the art, Ohm's law states that the current (I) through a conductor between two points is directly proportional to the potential difference or voltage (V) across the two points, and inversely proportional to the resistance (R) between them. The mathematical equation that describes this relationship is I=V/R, where I is the current through the resistance in units of amperes, V is the potential difference measured across the resistance in units of volts, and R is the resistance of the conductor in units of ohms. As such, unlike the prior art which maintains a constant magnetic field, by using the pot (e.g., rheostat) to vary its resistance R, it is possible to control the current I received by the electromagnet, thereby enabling variable strength of the device, and even enabling an "off" or "user is awake mode" (e.g., low power mode) state of the device when the device is not required (e.g., when the user is awake) by eliminating or substantially reducing the current I received by the electromagnet.

Notably, the determination of the appropriate current to generate the appropriate strength of the electromagnetic field may vary depending on the components used in the device, as well as the materials used to construct the electromagnet (e.g., whether or not it is a ferromagnetic-core electromagnet). In a preferred embodiment, the repulsion force provided by the devices' electromagnetic field should closely parallel or mimic the effect of air pressure provided by typical CPAP machines. For example, the titrated pressure is the pressure of air at which most (if not all) apneas and hypopneas have been prevented, and it is usually measured in centimeters of water (cm/H2O). The pressure required by most patients with sleep apnea ranges between 6 and 14 cm/H2O. A typical CPAP machine can deliver pressures between 4 and 20 cm/H2O. More specialized units can deliver pressures up to 25 or 30 cm/H2O. Generally, the basic mathematical formula for pressure P=F/A, where F is normal force and A is area. Accordingly, the appropriate strength of the electromagnetic field should be such that when a repulsion force is applied, it provides a similar force or effect as is provided by the pressure of a CPAP machine. The effective force between two electromagnets may be calculated using, e.g., the "Gilbert model", however, those skilled in the art recognize that other methods such as "real-world" trials may be used for the most accurate calculations.

Figure 5:
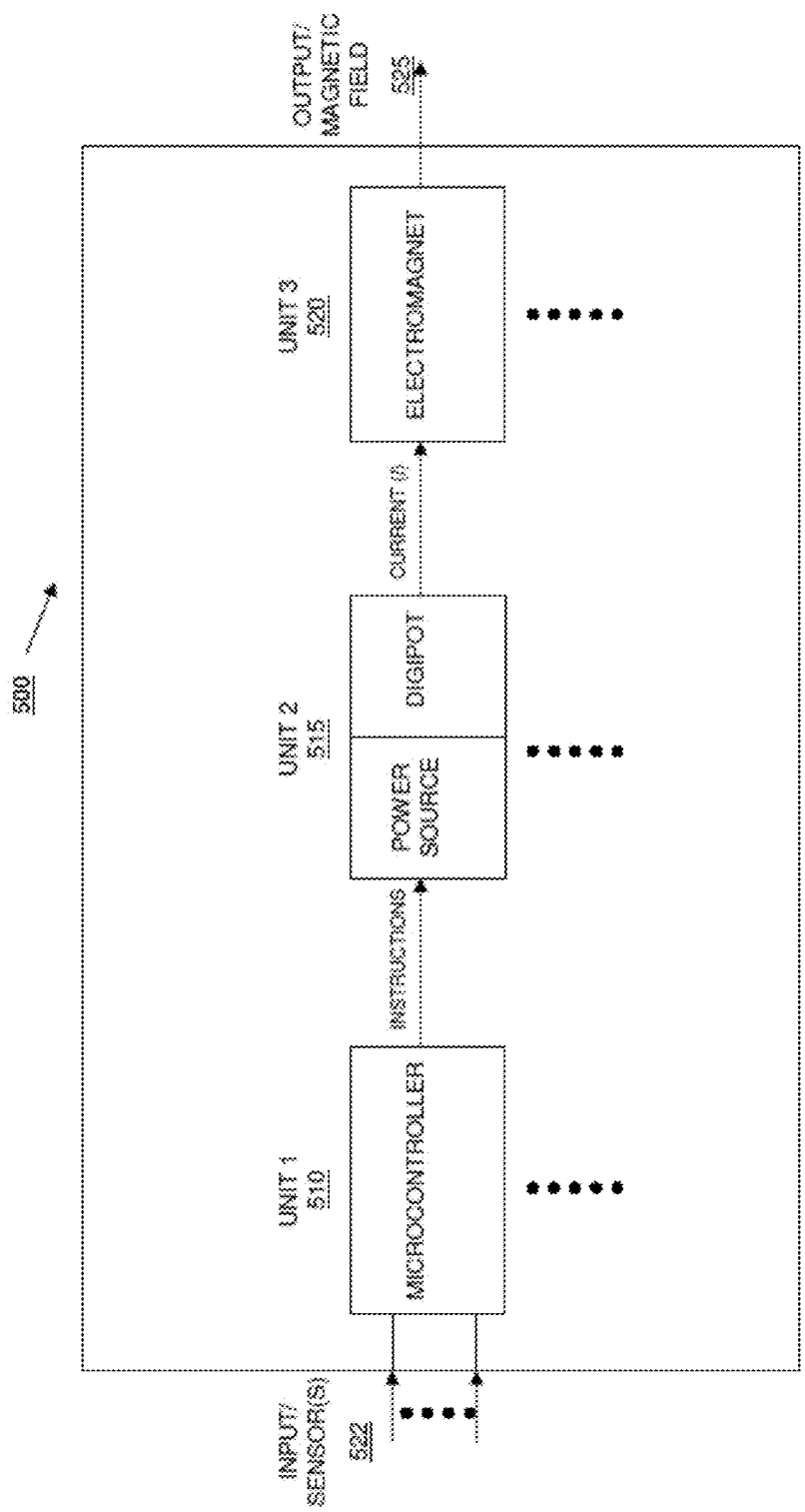
FIG. 5 is a schematic block diagram of an embodiment that may be advantageously used with the present disclosure.

FIG. 5 is a schematic block diagram of an embodiment that may be advantageously used with the present disclosure. As can be appreciated by those skilled in the art, device 500 may be placed in a biocompatible and corrosive resistant sleeve (case, sheath, capsule, etc.) to prevent interaction between the device and tissue/fluid of the body. Generally, a material may be considered biocompatible if the material does not cause a toxic or immunologic reaction to living tissue. The sleeve may illustratively be a stiffening and/or elastic (or non-elastic) plastic/mesh to uniformly distribute the repulsion force and to help stiffen soft tissue. The protective and biocompatible material may be selected among various types of materials, such as, e.g., titanium, silicone polymer, non-toxic epoxy, medical grade polyurethane, a U.V. curable medical acrylic co-polymer, polyvinyl chloride, ligament or connective tissue (of the patient), polytetrafluoroethylene, polycarbonate, polyester, polyethylene, hydrogel, stainless steel, etc. As can also be appreciated by those skilled in the art, the device may be implanted to the patient by known means, such as with sutures, pins, screws, allograft connective tissues (such as tendons, ligaments, cartilage, aponeuroses, skin attachment points of platysma), and/or bone attachment, etc.

As noted above, input/sensor 522 may comprise an accelerometer or microphone strategically placed in a location so as to detect vibrations, such as vibrations caused by snoring. According to one possible aspect of the embodiment, unit 1 (e.g., microcontroller (module)) 510 may receive a signal from input/sensor(s) 522 if snoring is detected. As noted above, an ADC may be used to convert the signal to a data type capable of being used by microcontroller 510. Illustratively, when microcontroller 510 receives a signal from sensor 522, a determination may be made as to whether or not the microcontroller should instruct unit 2 (e.g., power source/digipot (module(s))) 515 to output a current (or maintain its current output level if it is already outputting a current), thereby supplying (or maintaining) the current (I) necessary to create an electromagnetic field 525 from unit 3 (e.g., electromagnet (module)) 520. Alternatively, as can be appreciated by those skilled in the art, the determination as to whether or not to output a current may be made by any element (or unit) capable of making such a determination, such as the digipot. Accordingly, such a decision (or other decisions/determinations discussed throughout) described as being made by the microcontroller should be taken only as an example without limiting the scope of the disclosure. While the digipot is illustratively shown as part of the power source, those skilled in the art will recognize that the digipot may be located separately from the power source. Similarly, those skilled in the art will recognize that other elements/units/modules, combinations, configurations, and implementations of FIG. 5 (and any other described figures) capable of carrying out the functions of the disclosure may be used without departing from the scope of the current disclosure.

As will be discussed in FIG. 6, assume two devices (e.g., 500) are strategically placed to create a repulsion force between the two devices when each device is activated, thereby aiding to open the airways shown in FIGS. 1 and 2. Thus, depending on the desired strength of the magnetic field 525 (i.e., the repulsion force provided in response to two like poled magnetic fields), the digipot 515 may adjust its resistance and thereby the current provided to (e.g., both) strategically placed electromagnet(s) 520 according to program instructions stored in its NVRAM. For example, if the intensity of the vibrations sensed from sensor 522 reaches a first threshold intensity, in response, microcontroller 510 may alert the digipot to use a first resistance level resulting in a less intense current output to the electromagnet, thus producing a less intense repulsion force. However, if the intensity of the vibrations sensed from sensor 522 reaches a second threshold intensity, in response, microcontroller 510 may alert the digipot to use a second resistance level resulting in a higher current output to the electromagnet, thus producing a higher intensity repulsion force. Advantageously, similarly to how a CPAP machine may vary the air pressure required for adequate breathing, the present disclosure may also vary the intensity of the repulsion force. Additionally, should a patient suffering from OSA require a stronger or weaker force to alleviate the OSA, the digipot and/or microcontroller may be reprogrammed without requiring further surgery to remove the device to then alter or change the settings. For example, as is well known to those skilled in the art, the microcontroller and the digipot may be programmed and/or reprogrammed using, e.g., BLUETOOTH or other wireless device. As will be discussed below, the intensity of the electromagnetic field may also be self adjusted by the microcontroller due to the requirements of the user.

Figure 6:
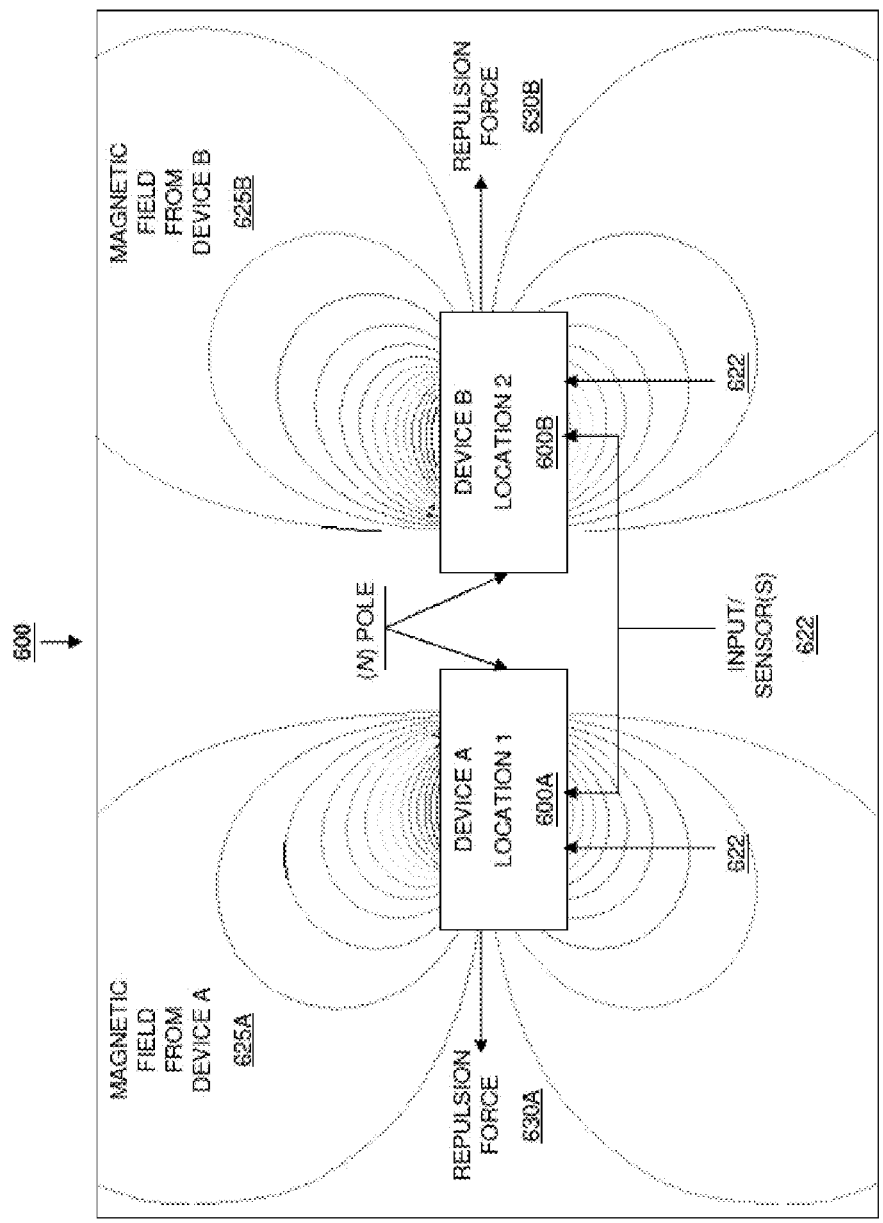
FIG. 6 is a schematic block diagram illustrating the interaction between two devices according to an embodiment of the present disclosure.

FIG. 6 is a schematic block diagram illustrating the interaction between two devices arranged and activated with similarly facing poles (e.g., north pole (N) as shown or south pole (S) not shown) to create a repulsion force to alleviate sleep apnea according to an embodiment of the present disclosure. Illustratively, each device 600A and 600B is strategically placed within opposing locations of the body to sufficiently alleviate OSA. For example, in reference to FIG. 9, location 1 of device 600A may be the base of the tongue, while location 2 of device 600B may be in the pharyngeal walls parallel to device 600A. As can be appreciated by those skilled in the art, the needs of each patient may be different, and thus require different locations to place each device. Other locations may comprise, for example, the vallecular, the hyoid bone and its attachments, the soft palate with uvula, the palatine tonsils with associated pillar tissue, and the epiglottis. In a preferred embodiment, the two locations may be placed in locations that provide the greatest widening of the airways using the least amount of repulsion force 630A and 630B from magnetic fields 625A and 625B respectively. Other locations, such as those described in the above noted U.S. Pat. No. 7,188,627, may also be used. While only a pair of devices 600A and 600B are shown, those skilled in the art will appreciate that multiple pairs of devices may be used. Alternatively, an uneven number of devices may be used to provide the most beneficial repulsion locations within the user. In a preferred embodiment, the number of devices used and the locations of the devices used should be determined on a patient-by-patient basis by a specialist (e.g., an Otolaryngologist).

Preferably, the repulsion force of 630A and 630B may be used to supplement the patient's natural tendency to maintain an open airway, rather than to replace it altogether. According to an embodiment of the disclosure, both devices may share the same input/sensor(s) 622 to act upon the same information. However, each device may also use its own exclusive sensors in addition to sharing other sensors, or each device may not share any sensors. Moreover, it is possible that the tissue surrounding the location of the devices may differ in resiliency or tolerance to the repulsion force. For example, the tissue of the posterior tongue may be able to handle more repulsion than the tissue of the pharyngeal wall. As such, it is explicitly contemplated that it may be beneficial for at least one device to produce a different electromagnetic field strength than the other device to widen the user's airways.

Figure 7:
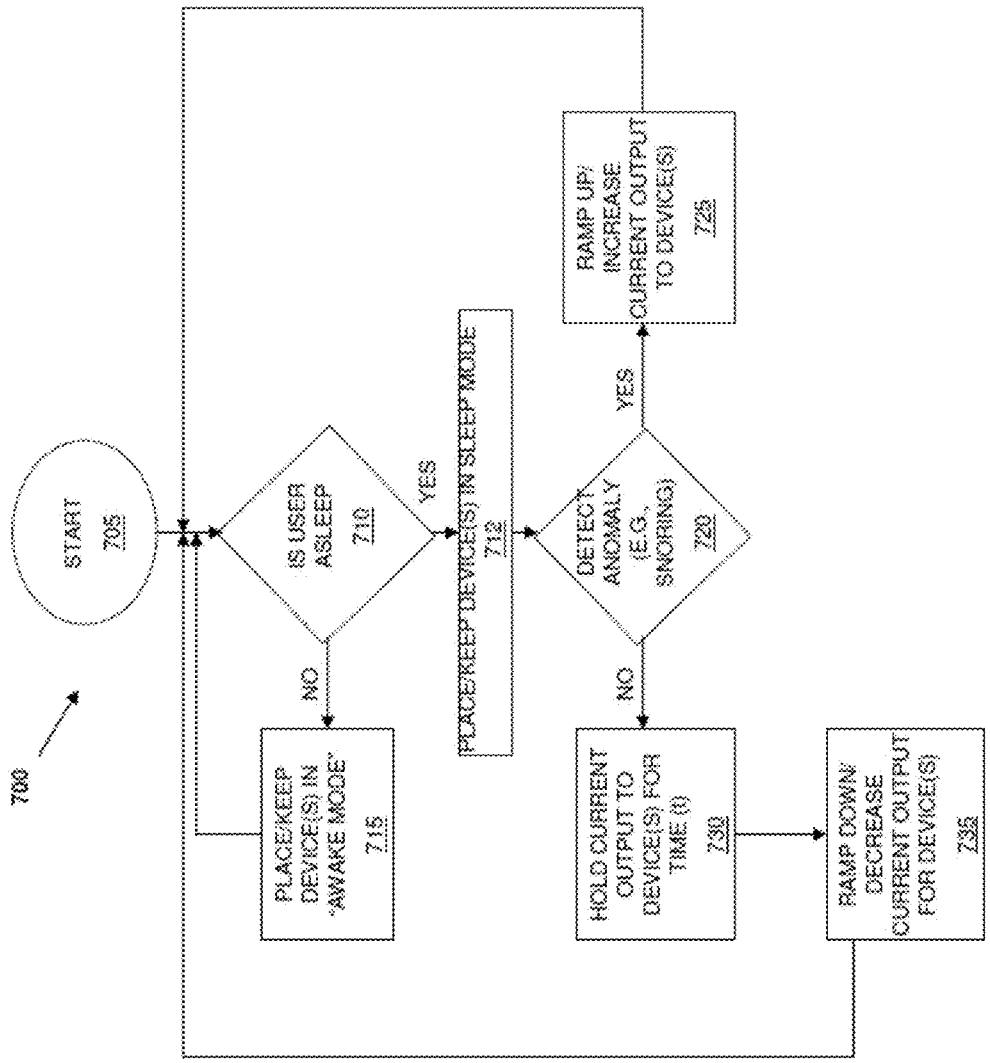
FIG. 7 is a flowchart illustrating a procedure for alleviating sleep apnea according to an embodiment of the present disclosure.

FIG. 7 is a flowchart illustrating a procedure for alleviating sleep apnea according to an embodiment of the present disclosure. The procedure 700 starts at step 705, and continues to step 710, where it is determined whether the user of the device is asleep. According to an embodiment, the device may only produce a desired electromagnetic field if the user is asleep. This may help to prevent producing an electromagnetic field when it is not needed, such as when the user is awake. To conserve battery life, a "sleep mode" may also be employed by the device when the user is awake, as known to those skilled in the art. However, to help avoid any confusion, the term "sleep mode" as generally and broadly used in the art to describe, e.g., a low power mode, will herein be referred to as "awake mode" to denote that the device has determined that the user is awake. For instance, when the user is awake and may not require the services of the device(s), the device may be placed in a low power mode (i.e., awake mode) to conserve energy. In contrast, when the user is asleep and may require the services of the device(s), the device may be placed in "sleep mode" to denote that the device has determined that the user is asleep. In one embodiment, it may be desirable only to activate the device when the user is sleeping. Therefore, according to the illustrative embodiment, different algorithms/formulas/variables may be employed (e.g., by the microcontroller) to make the determination as to whether the user of the device is awake or asleep. Such variables may be made taking into account, for example, data received from various sensors operatively connected to the microcontroller or operatively connected to any device making the determination. For instance, a user is typically lying in a horizontal position in bed when sleeping. As such, one of the sensors operatively connected to the microcontroller may be used to determine whether a user is horizontal (e.g., lying down). Another sensor may be used to determine whether a user's heart rate or breathing pattern is indicative that the user is sleeping. In other words, one illustrative algorithm/formula programmed at the microcontroller may be to determine whether the user is horizontal and/or whether the heart rate and/or breathing pattern is indicative of sleep. In the example, if any or all these variables indicate the user is sleeping, then it is likely that the user is in fact sleeping and the microcontroller may, e.g., place or keep the device in a sleep mode (step 712 discussed below). It will be appreciated by those skilled in the art that any algorithm and/or sensor input (e.g., accelerometer, myosensor, etc.) may be used by the microcontroller to contribute to a determination that a user is asleep.

If it is determined that the user is awake, then the device may be placed or kept in an "awake mode" in step 715. As noted above in one embodiment, the device may not produce the electromagnetic field in awake mode. As such, in an alternative embodiment, the device may simply note that the user is awake and use that information in determining whether or not to generate an electromagnetic field in response to detecting the anomaly, as discussed below. In another embodiment, the device may not even detect anomalies while in awake mode to conserve energy. According to another embodiment, even if the device is placed in awake mode, the device may periodically, e.g., every 30 minutes, check to determine if the user is asleep. If it is determined that the user of the device is asleep, then the procedure moves to step 712 where the device is placed (or kept/maintained) in "sleep mode" indicating that the user is asleep. From there, the procedure moves to step 720 where it is determined whether an anomaly or condition, such as a breathing anomaly or condition, is detected that warrants producing the electromagnetic field to help open the user's airways. For example, snoring may be a type of anomaly. As noted above, a microphone or accelerometer may be used as a vibration sensor to detect the vibrations associated with snoring. However, it will be appreciated by those skilled in the art that other types of anomalies may be detected using various other sensors, such as an air pressure sensor detecting a lack or degraded sense of breathing, and an O2 sensor detecting an irregular blood oxygen level brought on by an apneic episode(s). In a preferred embodiment, the device is used to prevent the occurrence of an apneic episode beforehand, rather than waiting for the apneic episode before helping to open the blocked airways. Typically, snoring may be a precursor to the total blockage of the airways producing an apneic episode. Thus, in the preferred embodiment, at least one of the anomalies detected would be the detection of snoring.

If an anomaly is detected, such as snoring, the microcontroller may signal for the power source (e.g., voltage or current source) to provide a current to the electromagnet to produce an electromagnetic field in step 725 as shown in FIG. 6. Illustratively, the current may be slowly "ramped up" incrementally step by step by a digipot to prevent a potentially uncomfortable sensation of an electromagnetic field brought upon by a sudden high supply of current. This may also help to prevent the user from awakening while generating the electromagnetic field. According to an embodiment of the present disclosure, the procedure then continuously determines if the snoring (or other anomalies) continue, and if so, the microcontroller may signal to the digipot to increase the output current to the electromagnet making the repulsion force of the electromagnetic field stronger, thus widening the airway, until the anomaly is no longer detected or has reached an acceptable level. In a preferred embodiment, a safeguard may be implemented to limit the maximum current that may be used to generate a maximum electromagnetic field and resulting repulsion force. For example, the maximum repulsion force may be comparable to the air pressure of 30 centimeter of water (cmH2O)

provided at the high end by a CPAP machine. Another safeguard that may be advantageously used is the ability to ensure that when the device(s) produce an electromagnetic field, that paired devices do not have an opposing electromagnetic field resulting in an undesired restriction force instead of the desired repulsion force. In a preferred embodiment, should such a situation be detected, the device should immediately eliminate at least one of the electromagnetic fields. The device may be configured to record such a situation in memory for subsequent review.

If an anomaly is not detected or is no longer detected due to a sufficient electromagnetic field, then the procedure moves to step 730 where the output of the current from the digipot to the electromagnet may be held or sustained for a predetermined amount of time (t) (e.g., 10 seconds). According to another aspect of the present disclosure, the microcontroller may store the amount of current required to prevent the detection of the anomaly for future reference or to be monitored by a doctor. Optionally, after the predetermined amount of time has elapsed, the microcontroller may signal to the digipot to decrease or slowly ramp down step by step the output current to the electromagnet in step 735 making the repulsion force of the electromagnetic field weaker. As a result, the device may specifically react to the varying needs of the user only when there is such a need and only with the appropriate amount of help required at that point in time. Advantageously, the device may adapt and react to the specific and "immediate" needs of the user, rather than having a one-size-fits-all approach as taught by the prior art.

Figure 8:
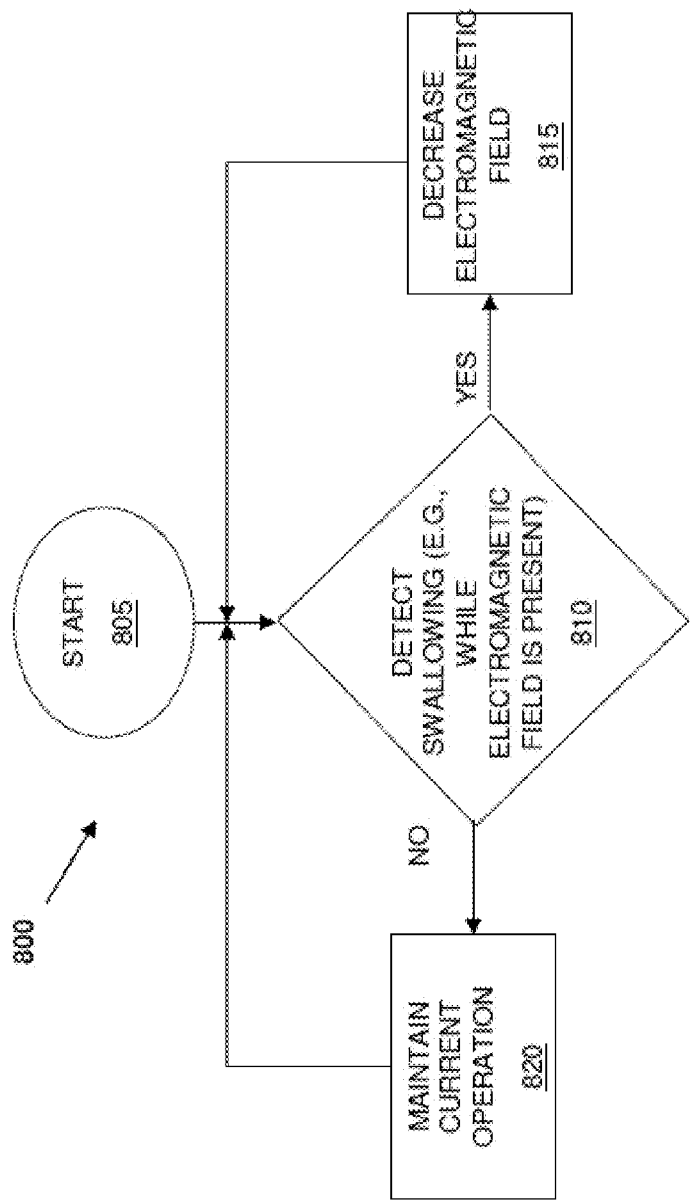
FIG. 8 is a flowchart illustrating a procedure for alleviating sleep apnea according to an embodiment of the present disclosure.

FIG. 8 is a flowchart illustrating a procedure for alleviating sleep apnea according to an embodiment of the present disclosure. The procedure 800 starts at step 805, and continues to step 810, where a determination is made as to whether or not swallowing (by the user) is detected while the user is asleep (i.e., the device is in sleep mode) or while an electromagnetic field is currently being generated by the device (e.g., from procedure 7 above). As noted above, this may be accomplished using the myosensors detecting action potentials from the muscles involved in the act of swallowing (e.g., skeletal tongue muscle, smooth muscles of the pharynx and esophagus, etc.). Illustratively, this determination may be made at any time while the user is asleep (i.e., while the device is in sleep mode). If swallowing is detected, the procedure moves to step 815 where the device may (e.g., temporarily) decrease the electromagnetic field, e.g., by eliminating or decreasing the current to the electromagnet. Advantageously, rather than having the user uncomfortably "fight" against the repulsion forces of the device to swallow, the microcontroller may be configured to detect when the user is swallowing (or about to swallow) and "immediately" eliminate or reduce the current to the electromagnet, thereby eliminating or reducing the electromagnetic field (and its repulsion force) that may be working against the user during the act of swallowing. While FIG. 8 is described as detecting the act of swallowing using myosensors, those skilled in the art will recognize that other detection types and sensors may be used. For example, positional sensors may be used to detect that the devices are being forced closer together, indicating that the user may be fighting the electromagnetic forces of the devices by swallowing. However, the use of myosensors may be a faster method of detecting that the user is swallowing or is about to swallow, since the action potentials of the swallowing muscles may be detected before all the necessary motor units necessary to swallow are recruited. If swallowing is not detected, the procedure moves to step 820 where the device maintains its current output (e.g., whatever current output was being provided at step 810).

Figure 1A:
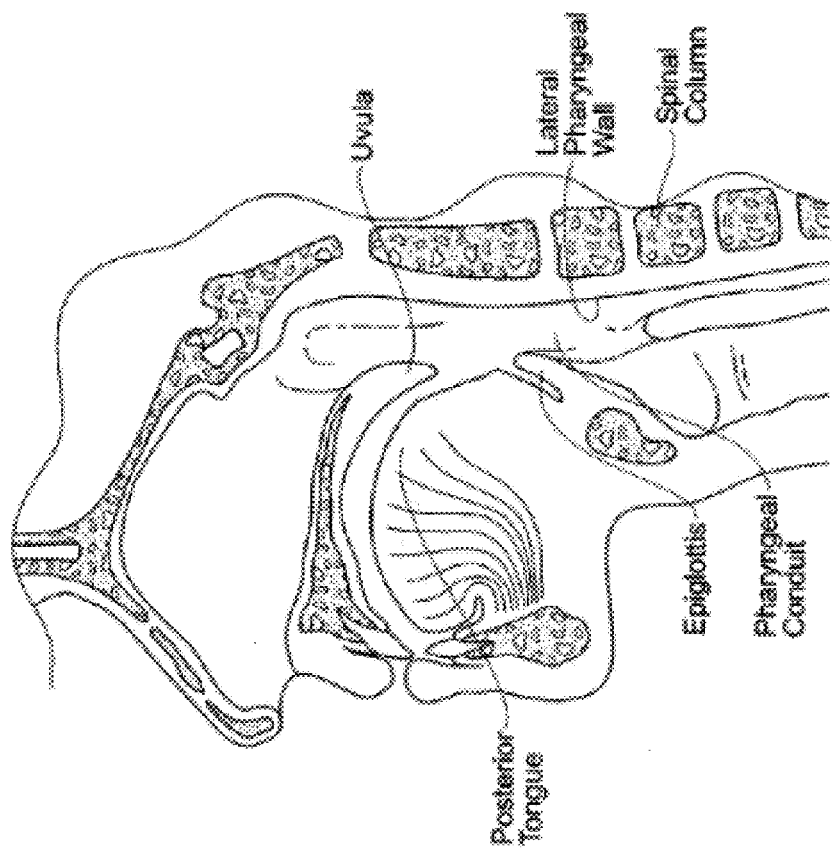
FIG. 1A is an anatomic view of a person with an open upper airway.
Figure 1B:
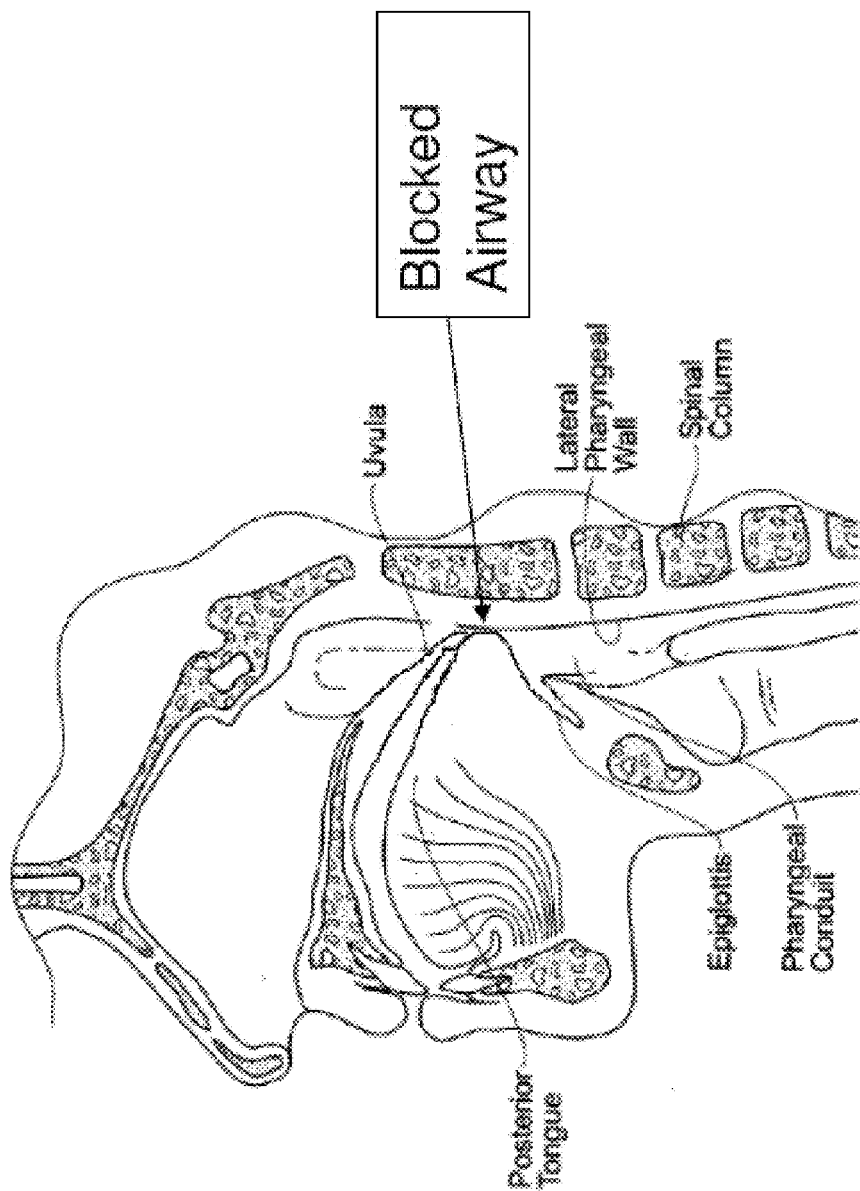
FIG. 1B is an anatomic view of a person with a completely obstructed upper airway.
Figure 9:
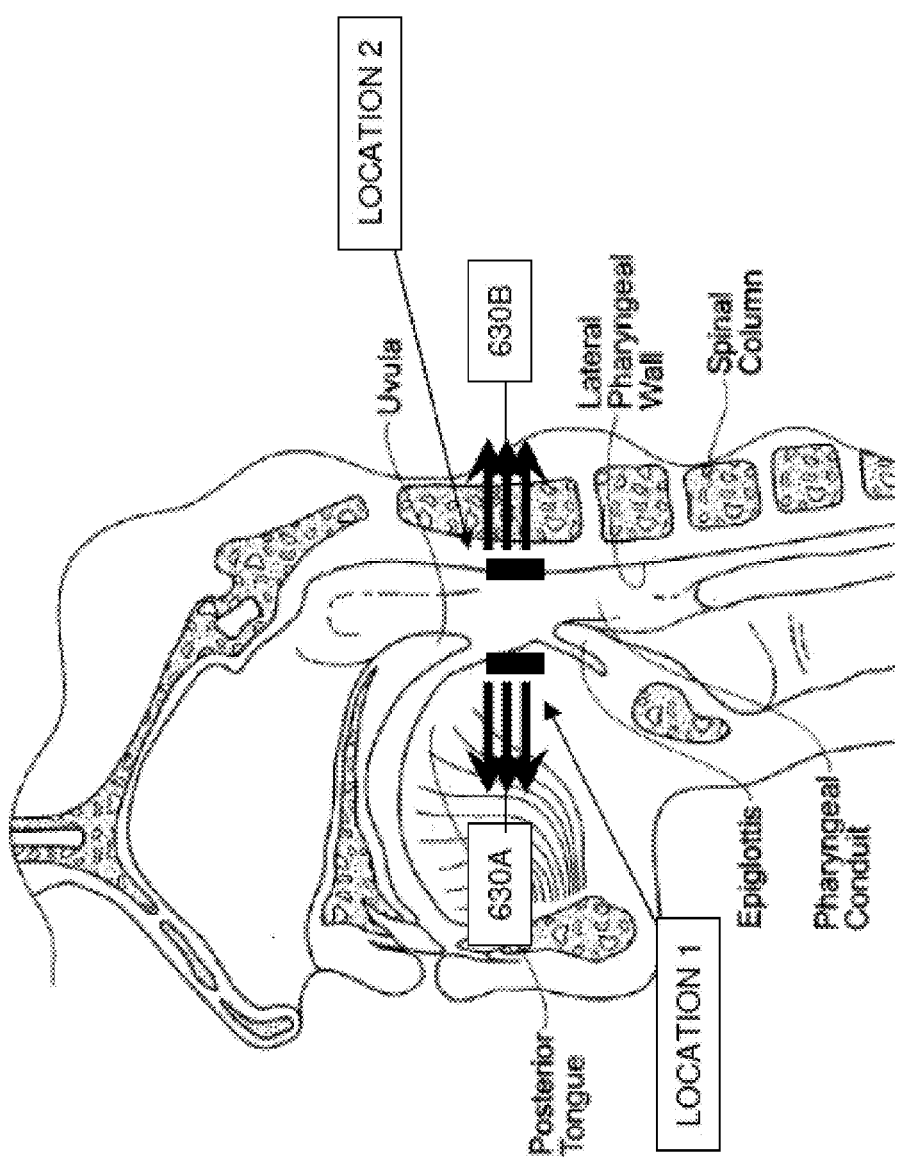
FIG. 9 is an anatomic view of a person with an open upper airway utilizing an embodiment of the present disclosure.

FIG. 9 is an anatomic view of a person with an open upper airway similar to FIG. 1 above, but with exemplary locations for implanting the device according to an embodiment of the present disclosure. As noted above in conjunction with FIG. 6, location 1 of device 600A may be the base of the tongue, while location 2 of device 600B may be in the pharyngeal walls parallel to device 600A. As can be appreciated by those skilled in the art, the needs of each patient may be different, and thus require different locations to place each device. Other locations may comprise, for example, the vallecular, the hyoid bone and its attachments, the soft palate with uvula, the palatine tonsils with associated pillar tissue, and the epiglottis. In a preferred embodiment, the two locations may be placed in locations that provide the greatest widening of the airways using the least amount of repulsion force 630A and 630B from magnetic fields 625A and 625B respectively. Preferably, the repulsion force of 630A and 630B may be used to supplement the patient's natural tendency to maintain an open airway, rather than to replace it altogether.

As can be appreciated by those skilled in the art, while the repulsion forces of the device may aid to open the user's airway, that same force applied against the human tissue may also "push" or constrict blood out of the tissue. If deprived of O2 provided by the blood for too long, cell death may result. One exemplary method to avoid the problem is to provide at least 2 pairs of devices and synchronously switch between using each pair. As such, while one pair of devices in one location is being used, the blood pushed out of the tissue from using the other pair of devices at a second location may return, and vice versa. Another exemplary method to avoid the problem is to have an automatically timed shut off, interrupt, "awake mode", etc., e.g., for 10 seconds every 20 seconds, to allow the blood to reenter the tissue. Notably, the location of the devices and the types of tissue affected may react differently to constricted blood over prolonged periods, thus, may vary the timing of the automatic shut off. Another exemplary method to avoid the problem, as discussed above, is to place the devices in a sleeve or pouch that may evenly distribute the repulsion force across the tissue. Such an even distribution may allow sufficient blood flow to the tissue thus obviating the problem altogether.

Advantageously, the novel intelligent device described herein provide a permanent, non-intrusive and non-cumbersome remedy to alleviate sleep apnea, without requiring one to wear a CPAP mask or other oral appliance while sleeping. Furthermore, unlike the prior art, the novel device may specifically react to the varying needs of the user only when there is such a need (e.g., when the user is asleep and/or when breathing is restricted during sleep) and only with the appropriate amount of help required at that point in time. Advantageously, the device may adapt and react to the specific and "immediate" needs of the user, rather than having a one-size-fits-all approach as taught by the prior art.

The foregoing description has been directed to specific embodiments of this disclosure. It will be apparent, however, that other variations and modifications may be made to the described embodiments, with the attainment of some or all of their advantages. For instance, it is expressly contemplated that at least some of the components and/or elements described herein may be implemented as software, including a computer-readable medium having program instructions executing on a computer, hardware, firmware, or a combination thereof. Accordingly this description is to be taken only by way of example and not to otherwise limit the scope of the disclosure. Therefore, it is the object of the appended claims to cover all such variations and modifications as come within the true spirit and scope of the disclosure.

What is claimed is:

1. A method for controlling a device to alleviate sleep apnea, comprising:
   determining that a breathing anomaly of the user is detected using a sensor operatively connected to the device; and
   widening the airway of the user in response to determining that the breathing anomaly is detected, wherein widening the airway of the user includes,
      maintaining a current to an electromagnet at a first level for a predetermined amount of time, and
      in response to maintaining the current for the predetermined amount of time, adjusting the current to the electromagnet to a second level.

2. The method of claim 1 further comprising varying the current to the electromagnet by a potentiometer to adjust the current to the electromagnet.

3. The method of claim 1 further comprising:
   determining that the user is asleep; and
   widening the airway of the user only in response to determining that the breathing anomaly is detected while the user is asleep.

4. The method of claim 3 wherein determining whether the user is asleep comprises at least one of determining the position of the device, determining a heart rate of the user by the device, and determining a breathing pattern of the user by the device.

5. The method of claim 1 further comprising increasing the current to the electromagnet to the first level until the breathing anomaly is no longer detected.

6. The method of claim 1 further comprising:
   determining that the user is awake; and
   in response to determining that the user is awake, placing the device in an awake mode, wherein widening of the airway of the user is precluded while the device is in the awake mode.

7. The method of claim 1 further comprising:
   detecting an act of swallowing by the user; and
   in response to detecting the act of swallowing by the user, decreasing the current to the electromagnet.

8. A system including a processor and a memory having a plurality of instructions stored thereon which, when executed by the processor, cause the processor to perform operations comprising, comprising:
   determining that a breathing anomaly of the user is detected using a sensor operatively connected to the device; and
   widening the airway of the user in response to determining that the breathing anomaly is detected, wherein widening the airway of the user includes,
      maintaining a current to an electromagnet at a first level for a predetermined amount of time, and
      in response to maintaining the current for the predetermined amount of time, adjusting the current to the electromagnet to a second level.

9. The system of claim 8 wherein the operations further comprise varying the current to the electromagnet by a potentiometer to adjust the current to the electromagnet.

10. The system of claim 8 wherein the operations further comprise:
    determining that the user is asleep; and
    widening the airway of the user only in response to determining that the breathing anomaly is detected while the user is asleep.

11. The system of claim 10 wherein determining whether the user is asleep comprises at least one of determining the position of the device, determining a heart rate of the user by the device, and determining a breathing pattern of the user by the device.

12. The system of claim 8 wherein the operations further comprise increasing the current to the electromagnet to the first level until the breathing anomaly is no longer detected.

13. The system of claim 8 wherein the operations further comprise:
    determining that the user is awake; and
    in response to determining that the user is awake, placing the device in an awake mode, wherein widening of the airway of the user is precluded while the device is in the awake mode.

14. The system of claim 8 wherein the operations further comprise:
    detecting an act of swallowing by the user; and
    in response to detecting the act of swallowing by the user, decreasing the current to the electromagnet.

15. A computer readable storage medium having a plurality of instructions stored thereon which, when executed by a processor, cause the processor to perform operations comprising:
    determining that a breathing anomaly of the user is detected using a sensor operatively connected to the device; and
    widening the airway of the user in response to determining that the breathing anomaly is detected, wherein widening the airway of the user includes,
       maintaining a current to an electromagnet at a first level for a predetermined amount of time, and
       in response to maintaining the current for the predetermined amount of time, adjusting the current to the electromagnet to a second level.

16. The system of claim 15 wherein the operations further comprise varying the current to the electromagnet by a potentiometer to adjust the current to the electromagnet.

17. The system of claim 15 wherein the operations further comprise:
    determining that the user is asleep; and
    widening the airway of the user only in response to determining that the breathing anomaly is detected while the user is asleep.

18. The system of claim 17 wherein determining whether the user is asleep comprises at least one of determining the position of the device, determining a heart rate of the user by the device, and determining a breathing pattern of the user by the device.

19. The system of claim 15 wherein the operations further comprise increasing the current to the electromagnet to the first level until the breathing anomaly is no longer detected.

20. The system of claim 15 wherein the operations further comprise:
    determining that the user is awake; and
    in response to determining that the user is awake, placing the device in an awake mode, wherein widening of the airway of the user is precluded while the device is in the awake mode.

21. The system of claim 15 wherein the operations further comprise:
    detecting an act of swallowing by the user; and in response to detecting the act of swallowing by the user, decreasing the current to the electromagnet.

\* \* \* \* \*